United States Patent [19]

Machado et al.

[11] Patent Number: 6,005,143
[45] Date of Patent: Dec. 21, 1999

[54] USE OF A MONOLITH CATALYST FOR THE HYDROGENATION OF DINITROTOLUENE TO TOLUENEDIAMINE

[75] Inventors: Reinaldo Mario Machado, Allentown; David Joseph Parrillo, Fleetwood; Richard Peter Boehme; Robert Roger Broekhuis, both of Allentown, all of Pa.

[73] Assignee: Air Products and Chemicals, Inc., Allentown, Pa.

[21] Appl. No.: 09/130,936

[22] Filed: Aug. 7, 1998

[51] Int. Cl.$^6$ ................................................ C07C 209/36
[52] U.S. Cl. ........................................ 564/423; 564/420
[58] Field of Search ................................ 564/420, 423, 564/372

[56] References Cited

U.S. PATENT DOCUMENTS

| | | | |
|---|---|---|---|
| 3,356,728 | 12/1967 | Cimerol et al. | 260/580 |
| 4,400,538 | 8/1983 | Chadwick | 564/423 |
| 4,520,124 | 5/1985 | Abe | 502/159 |
| 4,743,577 | 5/1988 | Schroeder et al. | 502/326 |
| 5,250,490 | 10/1993 | Ritscher et al. | 502/313 |
| 5,679,858 | 10/1997 | Langer et al. | 564/423 |

OTHER PUBLICATIONS

Hatziantoniou, et al., "The Segmented Two–Phase Flow Monolith Catalyst Reactor. An Alternative for Liquid–Phase Hydrogenation" Ind. Eng. Chem. Fundam vol. 23, No. 1, 82–88 (1984).

Hatziantoniou, et al., "Mass Transfer and Selectivity in Liquid–Phase Hydrogenation of Nitro Compounds in a Monolithic Catalyst Reactor with Segmented Gas–Liquid Flow", Ind. Eng. Chem Process Des. Dev., vol. 25, No. 4, 964–970 (1986).

*Primary Examiner*—Joseph K. McKane
*Attorney, Agent, or Firm*—Russell L. Brewer

[57] ABSTRACT

This invention relates to an improvement in a process for hydrogenating a nitroaromatic composition namely dinitrotoluene by contacting the dinitrotoluene with hydrogen in a reactor employing a monolith catalyst system. Broadly the improvement resides in the continuous, essentially solventless, adiabatic hydrogenation of dinitrotoluene to toluenediamine in a plug flow reactor system incorporating the monolith catalyst. The process generally comprises the steps:

introducing a feedstock comprised of dinitrotoluene and reaction product components continuously into the reactor and said feedstock having less that 30% by weight of a solvent, carrying out the hydrogenation of dinitrotoluene to toluenediamine under adiabatic conditions; and, continuously removing hydrogenated reaction product from the reactor.

13 Claims, 2 Drawing Sheets

HIGH VOID VOLUME FIXED BED CATALYST RECYCLE REACTOR SYSTEM

USE OF A MONOLITH CATALYST FOR THE HYDROGENATION OF DINITROTOLUENE TO TOLUENEDIAMINE

BACKGROUND OF THE INVENTION

The conventional industrial hydrogenation of dinitrotoluene, (dinitrotoluene), to toluenediamine, (toluenediamine), has been accomplished in a continuous three phase slurry stirred tank reactor. Dinitrotoluene is introduced in the stirred reactor along with a solvent such as methanol at a concentration of from 5 to 15 gram moles/m$^3$. Finely divided powder catalysts, especially nickel and palladium based catalysts, are suspended in the liquid phase stirred tank reactor and used as the primary catalysts to effect hydrogenation of the dinitrotoluene. Unfortunately, the use of these types of catalytic processes in the hydrogenation of dinitrotoluene result in processing difficulties, safety concerns, hygiene issues and environmental problems.

An option to the use of finely divided powder catalysts in stirred reactors has been the use of pelleted catalysts in fixed bed reactors. While this reactor technology does eliminate much of the handling and waste problems, a number of engineering challenges has not permitted the application of fixed bed reactor technology to the hydrogenation of nitroaromatic compounds in general and dinitrotoluene hydrogenation in particular. Controlling the overall temperature rise and temperature gradients in the reaction process, particularly in a dinitrotoluene process, has been one problem. Nitroaromatic compounds release more that 500 kJ/mole per nitro-functional group during hydrogenation. A second problem is that in fixed bed packed reactors there is a significant pressure drop due to the high flow rates required for nitroaromatic hydrogenation. A third problem is that liquid-gas distribution is problematic thus often leading to poor conversion and localized concentration gradients. These problems are cumulative in the production process and contribute to the considerable safety issues present in dinitrotoluene hydrogenation.

High void volume reactors incorporating monolith catalysts have been used in laboratory scale chemical processes including hydrogenation of nitroaromatics such as nitrobenzoic acid and m-nitrotoluene. These reactors have been operated at low conversion per pass with continuous recycle, thus simulating a batch process.

The following articles and patents are representative of catalytic processes employing monolith catalysts and processes in chemical reactions including the hydrogenation of nitroaromatics and other organic compounds.

Hatziantoniou, et al. in "The Segmented Two-Phase Flow Monolithic Catalyst Reactor. An Alternative for Liquid-Phase Hydrogenations,", Ind. Eng. Chem. Fundam., Vol. 23, No.1, 82–88 (1984) discloses the liquid phase hydrogenation of nitrobenzoic acid (NBA) to aminobenzoic acid (ABA) in the presence of a solid palladium monolithic catalyst. The monolithic catalyst consisted of a number of parallel plates separated from each other by corrugated planes forming a system of parallel channels having a cross sectional area of 1 mm$^2$ per channel. The composition of the monolith comprised a mixture of glass, silica, alumina, and minor amounts of other oxides reinforced by asbestos fibers with palladium metal incorporated into the monolith in an amount of 2.5% palladium by weight. The reactor system was operated as a simulated, isothermal batch process. Feed concentrations between 50 and 100 moles/m$^3$ were cycled through the reactor with less than 10% conversion per pass until the final conversion was between 50% and 98%

Hatziantoniou, et al. in "Mass Transfer and Selectivity in Liquid-Phase Hydrogenation of Nitro Compounds in a Monolithic Catalyst Reactor with Segmented Gas-Liquid Flow", Ind. Eng. Chem. Process Des. Dev., Vol. 25, No.4, 964–970 (1986) discloses the isothermal hydrogenation of nitrobenzene and m-nitrotoluene in a monolithic catalyst impregnated with palladium. The authors report that the activity of the catalyst is high and therefore mass-transfer is rate determining. Hydrogenation was carried out at 590 and 980 kPa at temperatures of 73° and 103° C. Again, less than 10% conversion per pass was achieved.

U.S. Pat. No. 4,520,124 discloses a process for producing catalytic structures in the form of sheets or honeycombs for the gas phase reduction of nitrogen oxides. A porous honeycomb structure is impregnated with titanium dioxide as a carrier material. The structure then is immersed in a solution containing a catalytically active oxide of copper, iron, vanadium, tungsten or molybdenum and then calcined to form the catalyst. Gas phase reduction of nitrogen oxides was effected in the presence of ammonia as a reducing agent.

U.S. Pat. No. 4,743,577 discloses metallic catalysts which are extended as thin surface layers upon a porous, sintered metal substrate for use in hydrogenation and decarbonylation reactions. In forming a monolith, a first active catalytic material, such as palladium, is extended as a thin metallic layer upon a surface of a second metal present in the form of porous, sintered substrate and the resulting catalyst used for hydrogenation, deoxygenation and other chemical reactions. The monolithic metal catalyst incorporates such catalytic materials such as palladium, nickel and rhodium, as well as platinum, copper, ruthenium, cobalt and mixtures. Support metals include titanium, zirconium, tungsten, chromium, nickel and alloys.

U.S. Pat. No. 5,250,490 discloses a catalyst made by an electrolysis process for use in a variety of chemical reactions such as hydrogenation, deamination, amination and so forth. The catalyst is comprised of a noble metal deposited, or fixed in place, on a base metal, the base metal being in form of sheets, wire gauze, spiral windirigs and so forth. The preferred base metal is steel which has a low surface area, e.g., less than 1 square meter per gram of material. Catalytic metals which can be used to form the catalysts include platinum, rhodium, ruthenium, palladium, iridium and the like.

U.S. Pat. No. 4,400,538 discloses the fixed bed catalytic hydrogenation of mononitrobenzene and dinitrobenzene in a stirred autoclave. The catalyst is an activated noble metal, e.g., palladium, iridium, rhodium, ruthenium or platinum and is in the form of a screen or coherent body such as perforated or fluted sheets, honeycomb structure, foils, wires, etc. Temperatures range from ~130° to 150° C.

U.S. Pat. No. 3,356,728 discloses the catalytic hydrogenation of aromatic polynitro compounds to aromatic polyamines via a slurry-phase catalyst system. Finely defined Raney nickel is the preferred catalyst.

U.S. Pat. No. 2,976,320 discloses a process for producing toluenediamine by the catalytic hydrogenation of dinitrotoluene utilizing an aqueous suspension of a palladium or platinum as the catalyst. The dinitro compound is dissolved in methanol.

BRIEF SUMMARY OF THE INVENTION

This invention relates to an improvement in a process for hydrogenating a nitroaromatic composition by contacting said nitroaromatic composition with hydrogen in a reactor employing a high void volume monolith catalyst system.

Broadly the improvement resides in the continuous hydrogenation of dinitrotoluene to toluenediamine via a plug flow reactor system incorporating the monolith catalyst. The process generally comprises the steps:

carrying out the hydrogenation of dinitrotoluene to toluenediamine under adiabatic conditions; and, introducing a feedstock comprised of dinitrotoluene and reaction product components continuously into the reactor, continuously removing hydrogenated reaction product from the reactor.

In a more particular form the improvement resides in the steps:

(a) establishing an inlet feed temperature of from 100° to 140° C., preferably 110°–130° C.;

(b) continuously feeding hydrogen and a dinitrotoluene containing feed to an inlet to the reactor containing the high void volume monolith catalyst;

(c) establishing a dinitrotoluene feed composition of from 0.5–3% by weight, preferably 1–2.5% by weight;

(d) continuously removing a toluenediamine/nitrotoluene reaction product from the reactor at an exit temperature above about 135° C. and generally less than about 180° C., preferably from 145°–165° C.;

(e) maintaining a conversion of at least 90% of the feed dinitrotoluene to toluenediamine per pass through the reactor; and, (f) recycling at least a portion of the toluenediamine/dinitrotoluene reaction product to the inlet of said reactor.

There are numerous advantages associated with the process and these include:

an ability to achieve excellent reaction rates through high gas-liquid and liquid/solid mass transfer;

an ability to effect hydrogenation of dinitrotoluene without the use of solvents thus eliminating some of the purification steps;

an ability to effect continuous hydrogenation of dinitrotoluene to toluenediamine without substantial byproduct production;

an ability to utilize monolith catalysts in a hydrogenation process thereby minimizing capital investment, while maintaining the advantages of fixed bed reactors and eliminating the disadvantage of slurry phase reactors;

an ability to generate high quality steam by virtue of adiabatic operation thus taking advantage of the heat of reaction;

an ability to achieve substantially higher production rates/volume catalytic reactor than conventional backmixed DNT hydrogenation reactors;

an ability to operate a hydrogenation process, plug flow, as in fixed bed reactors, but with low pressure drop characteristics; and, an ability to achieve excellent unit catalyst life through adiabatic operation of a reactor containing a high void volume monolith catalyst.

DETAILED DESCRIPTION OF THE INVENTION

Dinitrotoluene presents unique problems in its conversion to toluenediamine via catalytic hydrogenation. Dinitrotoluene is particularly sensitive to reaction conditions and, if present in concentrations>2% by weight in the reaction feed and in the reaction zone in conventional processes, a temperature excursion can lead to industrial explosion. Accordingly, dinitrotoluene, in contrast to nitroaromatics in general, has been hydrogenated at low concentration, e.g., <0.5% by weight at reaction temperatures of from 140° to 170° C. Solvents, such as methanol, have been included in the reaction medium to mitigate against temperature excursions by promoting hydrogenation.

The safety problems in dinitrotoluene hydrogenation have long been considered in commercial operations. For example, the general trend in commercial manufacture has been back mixed catalytic hydrogenation in stirred tank reactors employing dinitrotoluene concentrations of less than 0.2% by weight or in the region designated A in FIG. 1. At higher dinitrotoluene concentrations, especially with nickel based catalysts, the rate of dinitrotoluene hydrogenation can decline because the nitroaromatic compounds act to oxidize the nickel catalyst. Under high temperature reaction conditions, e.g., 150° to 170° C., as employed in backmixed hydrogenation vessels, catalyst deactivation can quickly lead to higher dinitrotoluene concentrations in the reaction medium which then can lead to a temperature excursion, and then, possibly to the types of explosions referred to above. That is a condition that must be avoided as illustrated by the decomposition data for dinitrotoluene in FIG. 2.

A high mass transfer rate in the reaction process is particularly critical because extended dinitrotoluene contact with the catalyst tends to cause catalyst deactivation. Achieving a high mass transfer rate in the hydrogenation of dinitrotoluene is difficult (six moles hydrogen are required for conversion of dinitrotoluene to toluenediamine) and further the high mass transfer rate is compounded by the relatively low hydrogen solubility in the toluenediamine reaction product. High mass transfer has been achieved in backmixed reactions, by increasing hydrogen pressure and effecting optimum sparging and agitation.

It has been found that dinitrotoluene can be continuously hydrogenated readily in a high void volume reactor having a void space>65% and sometimes>80% employing a monolith catalyst and yet accommodate safety issues presented by high inlet dinitrotoluene feed concentrations. Surprisingly, one can also effect conversion of dinitrotoluene to toluenediamine without concomitant catalyst deactivation and substantial byproduct formation if one adheres to a set of prescribed conditions. Adiabatic operation via plug flow is a key to the continuous hydrogenation process.

One key to the hydrogenation of dinitrotoluene is the use of a monolith catalyst which is sufficiently active to initiate or "kick off" the dinitrotoluene hydrogenation at low temperature (100°–140° C. and preferably from 100° to 120° C.)

to permit a significant temperature rise in the reactor through adiabatic operation. Such a catalyst should be capable of effecting a reaction rate of from >1.5 and preferably >2, gmole DNT/m$^3$ catalyst second at 130° C. and a hydrogen pressure of 1600 kPa. Adiabatic conditions and an active monolith catalyst component permit temperature acceleration throughout the reaction zone for continuous hydrogenation. A differing temperature profile from batch processes and from previous nitroaromatic hydrogenation processes employing a monolith catalyst allows for continuous hydrogenation. In addition, the differing reactor temperature profile provided by operating under adiabatic conditions allows for utilization of the heat of reaction to control reaction conditions and, surprisingly, stability of the reaction medium. Adiabatic hydrogenation of dinitrotoluene maintains stability of the reaction medium because of the immediate and continual formation of aminonitrotoluene. Aminonitrotoluene is an order of magnitude more stable than dinitrotoluene. Thus, as the dinitrotoluene reacts quickly to aminonitrotoluene prior to reaching exit reaction temperatures of 135° C. and above and generally less than 170° C., one can essentially avoid the safety problems associated with other processes and significant byproduct formation.

The feed to the reactor system is comprised of a mixture of toluenediamine, water, and dinitrotoluene and thus essentially non solvent, i.e., less than 30% by weight. By nonsolvent it is meant that the feedstock is comprised essentially of dinitrotoluene and a carrier comprised of dinitrotoluene hydrogenation reaction product components. In the backmixed hydrogenation of dinitrotoluene, and in some of the other procedures, a solvent (other than dinitrotoluene hydrogenation reaction products in which dinitrotoluene is soluble) is required for generating a hydrogenation feedstock, the common solvent being methanol. It is usually present in an amount of from 30 to 70% by weight of the feedstock. Of course, in the present process, solvents may be used, e.g., up to about 30% by weight of the feedstock but preferably less than 5% by weight and most preferably none is used. As is known from a backmixed operation, the use of solvents requires additional recovery steps and therefore such use should be avoided.

High dinitrotoluene feed concentrations and controlled flow rates through the high void volume reactor can be used in the hydrogenation process. The concentration of the dinitrotoluene in the feed typically is in the range designated B in FIG. 1 and is in contrast to the typical dinitrotoluene concentration (designated A) for the back mixed hydrogenation of dinitrotoluene. More specifically, the dinitrotoluene concentration in the feedstock is within a range to the reactor from 0.2 to 3%, preferably 1 to 2% by weight.

A key to reducing the quantity of byproducts produced in the hydrogenation process is control of the inlet temperature to the reactor at high dinitrotoluene concentrations. It is important to operate on the low side of the operable inlet temperatures, e.g., 100° to 120° C. at dinitrotoluene concentrations of from about 1 to 2% by weight dinitrotoluene. Temperatures greater than about 140° C. tend to permit dinitrotoluene to react with itself to produce unwanted byproducts. That is in addition to the safety problems that may be created (Note FIG. 2 which shows the high decomposition rate of dinitrotoluene at temperatures of 140° C. and above). Thus, inlet temperatures from 130° to 140° C. are best used when the dinitrotoluene feed concentration is from 0.5 to 1% by weight and inlet temperatures of 100° to 120° C. when dinitrotoluene concentrations range from 1 to 2% and slightly higher.

The adiabatic conditions for effecting hydrogenation of the dinitrotoluene to toluenediamine range are controlled to provide an exit temperature of from 135° to180° C. and particularly from about 145° to 165° C. By operating the reactor under adiabatic conditions and thus effecting a temperature rise through the reactor within a range of at least 20° C. to about 75° C. and preferably between 25° C. and 50° C., continuous hyrogenation may be effected, byproduct formation can be minimized and process safety enhanced.

In operation, the hydrogen pressure will range from about 1000 to 9000 kPa and typically from about 3000 to 6000 kPa. Because the dinitrotoluene is somewhat of a catalyst poison, catalyst activity is lengthened by operating at high hydrogen pressures to facilitate accelerated hydrogenation of the dinitrotoluene. It has been found that preferred conditions are such that the ratio of dinitrotoluene in parts per million by weight (ppm) divided by the total hydrogen pressure in kPa should be below 8, preferably below about 6. When the ratio begins to exceed 6, the amount of unreacted dinitrotoluene and byproduct in the reaction product from the monolith reactor may become unacceptable leading to greater catalyst deactivation and to greater load on the polishing reactor. The former is largely a function of residence time while the latter is a function of inlet temperature. A ratio of from about 2–6 (dinitrotoluene ppm/kPa) is preferred.

The superficial liquid and gas velocities in the monolith channels are maintained to effect a 90% or greater conversion per pass of dinitrotoluene. Typically, the superficial velocity through the monolith ranges between 0.1 to 1 meter per second with residence times of from 10 to 120 seconds in order to achieve such conversion. As dinitrotoluene concentration increases it is sometimes necessary to increase the residence time but often that results in increased levels of byproducts.

Monolith catalysts employed in the adiabatic process described herein consist of a porous substrate or base metal substrate coated with a catalytic metal. Often the monoliths are based upon a honeycomb of long narrow capillary channels, circular, square or rectangular, whereby gas and liquid are co-currently passed through the channels under a laminar flow regime. The flow of gas and liquid in these confined channels and under these conditions promotes "Taylor" flow with bubbles of gas squeezing past the liquid. This capillary action promotes very high initial gas-liquid and liquid-solid mass transfer. Accordingly, a concentrated dinitrotoluene feed can be quickly reduced in dinitrotoluene concentration, thus creating a highly efficient and intensive reactor with a significantly reduced pressure drop vis-a-vis a fixed bed reactor. The pressure drop within an effective monolith reactor can range from 2 kPa/m to 200 kPa/m for combined gas/liquid superficial velocities between 0.1 to 2 meters/second for 50% gas holdup in a monolith reactor having 400 CPI (cells per square inch). Typical dimensions for a honeycomb monolith range from cell wall spacings of from 1 to 10 mm between the plates. Alternatively, the monolith may have from 100 to 600 CPI. Channels may be square, hexagonal, circular, elliptical, etc. in shape.

Catalytic metals suited for the hydrogenation of dinitrotoluene are impregnated or directly coated onto the monolithic substrate or from a washcoat which has been deposited onto the monolith. The catalytic metals include those Group VI and VIII metals of the periodic table and conventionally used in the hydrogenation of dinitrotoluene. Examples of catalytic metal components include cobalt, Raney or sponge nickel, palladium, platinum, copper, and so forth. Often a mixture of metals are employed, one example being palladium and nickel. For a monolith catalyst impregnated with a washcoat the composition of catalytic metals are typically identified as a weight percent within the washcoat itself. The washcoat may be applied in an amount of from 1 to 20% of the monolith total weight. Typical catalyst metal loadings, then, range from 0.1 to 25% by weight and preferably from 1 to 10% by weight of the wash coat. The catalytic metals may be incorporated into the monolith in a manner generally recognized by the art. Incipient wetness from a salt solution of the catalytic metal is one example of a method for incorporating a metal catalytic component on the monolith substrate or via the washcoat. A preferred monolith catalyst employs a mixture of palladium and nickel, the concentration range based on a 10% washcoat being from 0.5 to 1.5% palladium and from 5 to 20% nickel.

Figure 1:
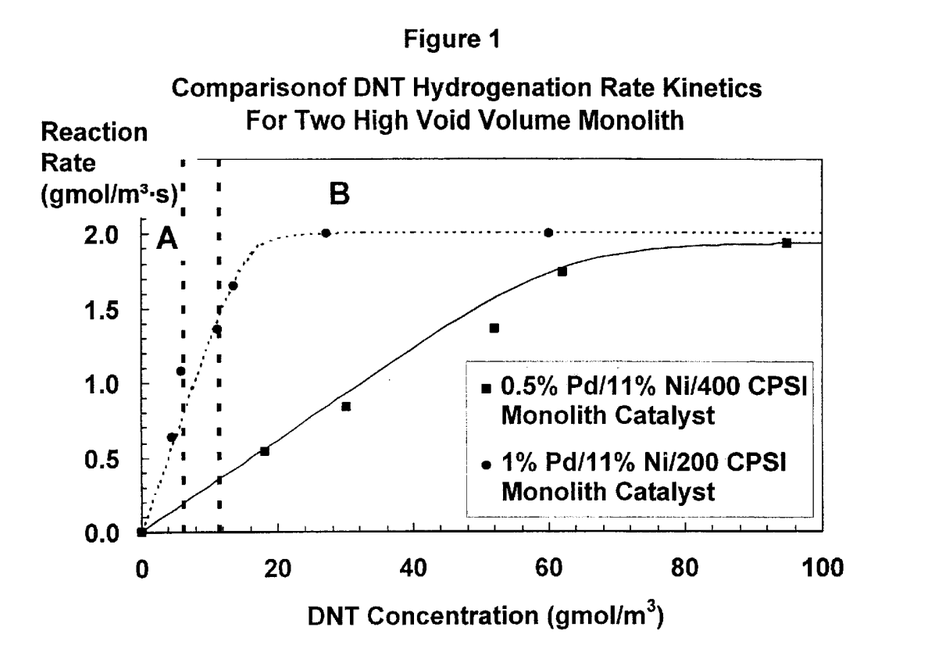
FIG. 1 is a plot of the hydrogenation rate versus concentration for a monolith catalyst reactor, the catalyst employing silica washcoats with 0.5% palladium and 11% nickel at 400 square cells per square inch (CPI) and plot of the hydrogenation rate verses concentration for a monolith catalyst reactor, the catalyst employing silica washcoats with 1% Pd and 11% Ni with 200 cells per square inch.
Figure 2:
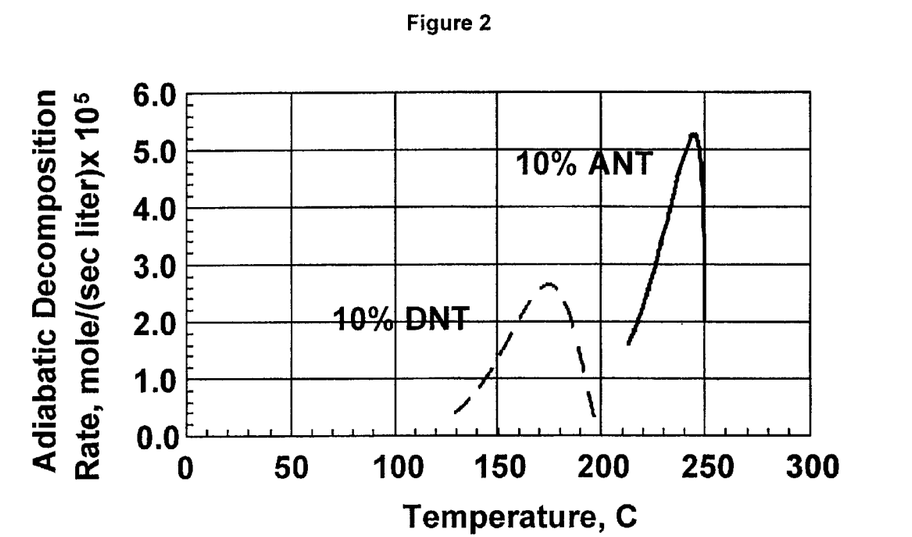
FIG. 2 is a plot of the adiabatic decomposition rate for dinitrotoluene, dinitrotoluene and aminonitrotoluene, (ANT) in a solution of 63% toluenediamine and 37% water as a function of temperature.

Although not intending to be bound by theory, the process design is such that the dinitrotoluene is introduced at concentrations approaching the plateau of the reaction rate curve where the reaction rate is highest (area B of FIG. 1). Decomposition of DNT is minimized by utilizing a reduced inlet feed temperature. As the feedstock proceeds through the high void volume reactor containing the monolith catalyst and one maintains a ratio of dinitrotoluene to hydrogen pressure (ppm to $H_2kPa$) sufficiently low, 2–6, the temperature of the stream as it proceeds through the reactor bed increases this driving the reaction toward completion and this is done without substantial byproduct production. Because of the heat generated, dinitrotoluene is converted in a single pass to conversions greater than 90%. Adiabatic operation and plug flow operation of the monolith reactor permits enhanced safety because there is a corresponding increase in aminonitrotoluene and toluenediamine concentration in the stream as it moves through the reactor an increases in temperature. Thus, by maintaining the inlet temperature of the feed at the lowest point in the overall reactor system and hydrogen concentration (pressure) sufficiently high to effect essentially instantaneous hydrogenation of the dinitrotoluene, coupled with the high dinitrotoluene concentration one can enhance continuous production through adiabatic operation.

Figure 3:
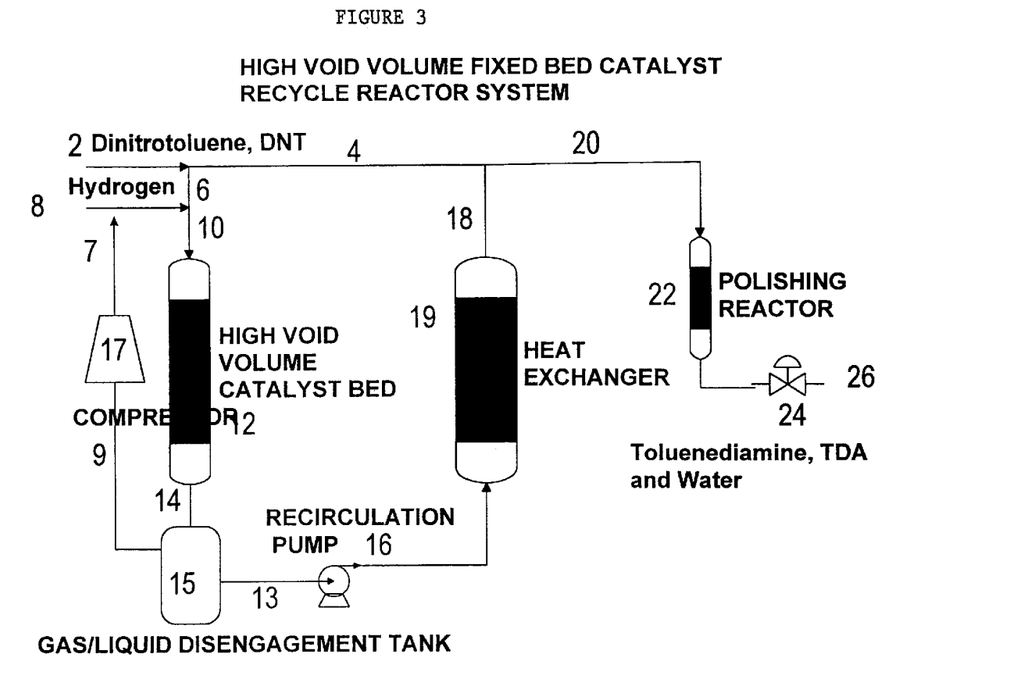
FIG. 3 is a flow sheet of the hydrogenation process for producing toluenediamine from dinitrotoluene in a high void volume reactor incorporating a monolith catalyst.

To facilitate an understanding of the process, reference is made to FIG. 3. The process for the hydrogenation of dinitrotoluene to form toluenediamine comprises feeding a dinitrotoluene through line 2 for combination with a carrier comprised of hydrogenation reaction product. The carrier is introduced to the dinitrotoluene or via line 4, thereby generating a feed composition comprising from about 0.2 to 3% by weight dinitrotoluene, preferably between 1 and 2%. The feed is then conveyed via line 6 where it is combined with hydrogen via line 8 to generate an inlet feed which is introduced through line 10 to a high void volume catalyst bed 12. Although the inlet is shown as an upper portion of the high void volume catalyst bed 12, feed can also be introduced at the bottom of the bed and passed upwardly through the bed.

High void volume catalyst bed 12 is fitted with a monolith catalyst having a 10% by weight of an alumina washcoat applied thereon, 400 CPI (square shape), the wash coat containing 1% palladium and 10% nickel based upon the weight of the washcoat. The feed stock introduced via line 10 is preheated to a temperature preferably between about 100° to 120° C. and pressurized to a operational pressure ranging from about 1600 to 8000 kPa, typically, 3000 to 6500 kPa. The two phase mixture of hydrogen and liquid dinitrotoluene/dinitrotoluene hydrogenation reaction product is passed through the monolith catalyst under adiabatic conditions. The heat of reaction causes the temperature of the feed stock to rise as it passes from one end of the reactor to the other and depending upon feed concentration, the preferred final exit temperature will range between 145° and 165° C. The elevated temperature enhances the rate of reaction per unit volume of the catalyst and leads to a corresponding decrease in the dinitrotoluene concentration as it proceeds from the inlet to outlet. The hydrogenation reaction product is removed via line 14 where the excess hydrogen is disengaged from the liquid hydrogenation product in disengagement tank 15. The liquid product is removed via line 13 where it is pumped via recirculation pump 16 through a shell and tube heat exchanger. Heat is removed from the hydrogenation reaction product and recovered as high pressure steam.

The cooled hydrogenation reaction product is removed from the shell and tube heat exchanger via line 18 and split with one portion returned to the reactor section of the process via line 4 and the other removed via line 20 to a polishing reactor 22 and then reduced in pressure through valve 24. The polishing reactor is provided (e.g., conventional stirred tank reactor with suspended nickel catalyst or a small monolith reactor) to complete the hydrogenation of unreacted dinitrotoluene in the hydrogenation reaction product. There is generally unreacted dinitrotoluene in the reaction product which is converted to toluenediamine at low temperature. This final processing is referred to as polishing and completes the conversion of residual dinitrotoluene to essentially 100%. The resulting mixture of toluenediamine and water is removed via line 26 where it is charged to a distillation recovery system not shown. The procedure for recovering toluenediamine from the hydrogenation reaction product is conventional to that employed in the prior art.

The following examples are intended to illustrate various embodiments of the invention and are not intended to restrict the scope thereof.

EXAMPLE 1

Hydrogenation Of Toluenediamine In High Void Volume Reactor

The reactor is comprised of a cylindrical monolith reactor bed, approximately 5 meters high and 0.5 meters in diameter with a total volume of 1.00 $m^3$. The catalyst bed is made from a commercial 400 CPI cordierite monolith support having square shaped cells with a 10% alumina washcoat and a catalyst metal loading of 10% nickel and 1% palladium based on the washcoat.

The reactor system is set up similar to FIG. 3 with the excess hydrogen gas being recycled to the inlet of the reactor using a compressor; no polishing reactor is used for purposes of demonstrating this process. The dinitrotoluene feed is continuously fed as a molten liquid and no solvent is employed. The toluenediamine and water product are continuously removed. Hydrogen is fed in excess of the stoichiometric requirement.

A variety of process conditions are varied including feed rate, recycle ratio, pressure inlet temperature, exit temperature. The reactor design is simulated to provide an estimated gas/liquid mass transfer rate of 10 and a mass transfer rate of 1. These conditions are set forth in Table 1. The results with respect to conversion of dinitrotoluene to toluenediamine, byproducts and conversion are set forth in Table 2.

Table 1:

Hydrogenation Conditions

Catalyst activity is defined as the slope of the linear low concentration range of the reaction rate (gmole dinitrotoluene/($m^3$ monolith catalyst second)) vs. the concentration (gmole dinitrotoluene/($m^3$ liquid phase)) as illustrated in Region A of FIG. 1.

To aid in understanding the layout of the data in the tables, the following is provided:

Runs 1–3 show the effects of concentration of inlet dinitrotoluene.

Runs 4–6 are a repeat of Runs 1–3 but at higher pressure.

Runs 7–9 are a repeat of Runs 4–6 but at reduced residence time.

Run 10 is essentially a repeat of Run 8 but at reduced residence time and a higher pressure.

Runs 11–14 show the effect of increased inlet temperature and a corresponding increase in pressure at feed concentrations similar to Run 1–3.

Runs 16–31 show the general effect of a mass transfer coefficient of 1 compared to Runs 1–15 and 31–34 which are based upon a mass transfer coefficient 1–10.

Runs 15–19 are similar to Runs 1–3 and Run 12, but at an intermediate pressure.

Runs 20–23 are similar to Runs 4–6, but at a reduced gas/liquid mass transfer rate.

Runs 24–27 show the effects of inlet increased temperature at high pressure with reduced gas/liquid mass transfer at a DNT concentration of ~1.3% by weight.

Run 28 shows the effect of a low inlet temperature and low inlet DNT concentration at low gas-liquid mass transfer. (Compare to Run 6.)

Runs 31–34 show the effect of residence time and high pressure at moderate dinitrotoluene concentrations, i.e., from about 1.4 to 3.2%.

TABLE 1

| Run | Inlet Feed Rate mole/($m^3$ sec) | Inlet Temp. °C. | Inlet dinitrotoluene conc. mole/$m^3$ | Inlet dinitrotoluene Conc. ppm | Total Pressure kPa | Inlet Ratio dinitrotoluene/ Pressure ppm/kPa | Residence Time seconds | gas/liq. mass transfer coeff. kla seconds$^{-1}$ | Catalyst Activity seconds$^{-1}$ |
|---|---|---|---|---|---|---|---|---|---|
| 1 | 2.00 | 110 | 237 | 43134 | 1600 | 27.0 | 119 | 10.0 | 0.3 |
| 2 | 2.00 | 110 | 142 | 25844 | 1600 | 16.2 | 71 | 10.0 | 0.3 |
| 3 | 2.00 | 110 | 71 | 12922 | 1600 | 8.1 | 36 | 10.0 | 0.3 |
| 4 | 2.00 | 110 | 237 | 43134 | 4800 | 9.0 | 119 | 10.0 | 0.3 |
| 5 | 2.00 | 110 | 142 | 25844 | 4800 | 5.4 | 71 | 10.0 | 0.3 |
| 6 | 2.00 | 110 | 71 | 12922 | 4800 | 2.7 | 36 | 10.0 | 0.3 |
| 7 | 6.00 | 110 | 237 | 43134 | 4800 | 9.0 | 40 | 10.0 | 0.3 |
| 8 | 6.00 | 110 | 144 | 26208 | 4800 | 5.5 | 24 | 10.0 | 0.3 |
| 9 | 6.00 | 110 | 76 | 13832 | 4800 | 2.9 | 12 | 10.0 | 0.3 |
| 10 | 9.00 | 110 | 150 | 27300 | 6400 | 4.3 | 16 | 10.0 | 0.3 |
| 11 | 2.00 | 120 | 71 | 12922 | 1600 | 8.1 | 36 | 10.0 | 0.3 |
| 12 | 2.00 | 130 | 71 | 12922 | 1600 | 8.1 | 36 | 10.0 | 0.3 |
| 13 | 2.00 | 130 | 71 | 12922 | 4800 | 2.7 | 36 | 10.0 | 0.3 |
| 14 | 2.00 | 140 | 71 | 12922 | 4800 | 2.7 | 36 | 10.0 | 0.3 |
| 15 | 2.00 | 110 | 237 | 43134 | 3200 | 13.5 | 119 | 1.0 | 0.3 |
| 16 | 2.00 | 110 | 142 | 25844 | 3200 | 8.1 | 71 | 1.0 | 0.3 |
| 17 | 2.00 | 110 | 72 | 13104 | 3200 | 4.1 | 36 | 1.0 | 0.3 |
| 18 | 2.00 | 120 | 72 | 13104 | 3200 | 4.1 | 36 | 1.0 | 0.3 |
| 19 | 2.00 | 130 | 72 | 13104 | 3200 | 4.1 | 36 | 1.0 | 0.3 |
| 20 | 2.00 | 110 | 71 | 12922 | 4800 | 2.7 | 36 | 1.0 | 0.3 |
| 21 | 2.00 | 110 | 142 | 25844 | 4800 | 5.4 | 71 | 1.0 | 0.3 |
| 22 | 2.00 | 110 | 237 | 43134 | 4800 | 9.0 | 119 | 1.0 | 0.3 |
| 23 | 2.00 | 110 | 142 | 25844 | 6400 | 4.0 | 72 | 1.0 | 0.3 |
| 24 | 2.00 | 110 | 71 | 12922 | 6400 | 2.0 | 36 | 1.0 | 0.3 |
| 25 | 2.00 | 120 | 71 | 12922 | 6400 | 2.0 | 36 | 1.0 | 0.3 |
| 26 | 2.00 | 130 | 71 | 12922 | 6400 | 2.0 | 36 | 1.0 | 0.3 |
| 27 | 2.00 | 140 | 71 | 12922 | 6400 | 2.0 | 36 | 1.0 | 0.3 |
| 28 | 3.00 | 110 | 73 | 13286 | 4800 | 2.8 | 24 | 1.0 | 0.3 |
| 29 | 3.00 | 110 | 143 | 26026 | 4800 | 5.4 | 48 | 1.0 | 0.3 |
| 30 | 3.00 | 100 | 143 | 26026 | 4800 | 5.4 | 48 | 1.0 | 0.3 |
| 31 | 12.00 | 120 | 141 | 25662 | 8000 | 3.2 | 12 | 10.0 | 0.5 |
| 32 | 12.00 | 120 | 141 | 25662 | 6400 | 4.0 | 15 | 10.0 | 0.5 |

TABLE 1-continued

| Run | Inlet Feed Rate mole/(m³ sec) | Inlet Temp. °C. | Inlet dinitrotoluene conc. mole/m³ | Inlet dinitrotoluene Conc. ppm | Total Pressure kPa | Inlet Ratio dinitrotoluene/ Pressure ppm/kPa | Residence Time seconds | gas/liq. mass transfer coeff. kla seconds$^{-1}$ | Catalyst Activity seconds$^{-1}$ |
|---|---|---|---|---|---|---|---|---|---|
| 33 | 12.00 | 120 | 178 | 32396 | 6400 | 5.1 | 30 | 10.0 | 0.5 |
| 34 | 6.00 | 140 | 78 | 14200 | 6400 | 2.2 | 13 | 10.0 | 0.5 |

TABLE 2

| Run | Exit Temp. °C. | Exit dinitro- toluene Conc. ppm | dinotrotoluene Conversion/Pass % | Final dinitrotoluene Yield to toluenediamine % | By- products wt % |
|---|---|---|---|---|---|
| 1 | 180 | 0 | 100.0% | 83.7% | 16.3 |
| 2 | 159 | 2 | 100.0% | 97.4% | 2.6 |
| 3 | 135 | 49 | 99.6% | 99.5% | <0.5 |
| 4 | 187 | 0 | 100.0% | 91.4% | 8.6 |
| 5 | 160 | 0 | 100.0% | 99.0% | 1.0 |
| 6 | 135 | 1 | 100.0% | 99.5% | <0.5 |
| 7 | 187 | 50 | 99.9% | 91.4% | 8.6 |
| 8 | 160 | 345 | 98.7% | 98.9% | 1.0 |
| 9 | 135 | 975 | 99.8% | 99.5% | <0.5 |
| 10 | 150 | 1463 | 94.6% | 98.8% | 1.0 |
| 11 | 145 | 47 | 99.6% | 99.3% | 0.7 |
| 12 | 155 | 43 | 99.7% | 98.3% | 1.7 |
| 13 | 155 | 1 | 100.0% | 99.4% | 0.6 |
| 14 | 165 | 1 | 100.0% | 98.5% | 1.5 |
| 15 | 179 | 0 | 100.0% | 82.2% | 17.8 |
| 16 | 159 | 25 | 99.9% | 96.9% | 3.1 |
| 17 | 135 | 153 | 98.8% | 99.7% | <0.5 |
| 18 | 145 | 145 | 98.9% | 99.2% | 0.8 |
| 19 | 155 | 128 | 99.0% | 98.0% | 2.0 |
| 20 | 135 | 10 | 99.9% | 99.8% | <0.5 |
| 21 | 160 | 0 | 100.0% | 97.9% | 2.1 |
| 22 | 182 | 0 | 100.0% | 85.6% | 14.4 |
| 23 | 160 | 0 | 100.0% | 98.4% | 1.6 |
| 24 | 135 | 3 | 100.0% | 99.8% | <0.5 |
| 25 | 145 | 3 | 100.0% | 99.6% | <0.5 |
| 26 | 155 | 3 | 100.0% | 99.0% | 1.0 |
| 27 | 165 | 3 | 100.0% | 97.7% | 2.3 |
| 28 | 135 | 372 | 97.2% | 99.7% | <0.5 |
| 29 | 159 | 116 | 99.6% | 97.8% | 2.2 |
| 30 | 150 | 137 | 99.5% | 99.1% | 0.9 |
| 31 | 169 | 296 | 98.8% | 99.0% | 1.0 |
| 32 | 166 | 3 | 100.0% | 99.1% | 0.9 |
| 33 | 181 | 0 | 100.0% | 97.0% | 3.0 |
| 34 | 167 | 46 | 99.7% | 99.0% | 1.0 |

A few observations can be made from the runs reported in Tables 1 and 2, and that is that byproduct formation is directly proportional to inlet DNT concentration and inlet temperature. When the concentration of DNT exceeds about 3% by weight, byproduct formation is too high. This is true even with increased hydrogen pressure which would promote gas transfer and also with reduced residence time (Note Runs 1, 4, 7, and 22).

Runs 1 through 6 show the relationship of inlet dinitrotoluene concentration to exit temperature by virtue of adiabatic operation. The effect of increased pressure does not substantially effect exit temperature, but does result in reduced byproduct formation.

Runs 2, 3, 5, and 6 show clearly that byproduct levels of less than 3% and preferably less than 1% can be achieved by adiabatic operation at inlet DNT concentrates of ~2.5% and less. The effect of dinitrotoluene concentration to pressure is noted from these few examples and is expressed in the dinitrotoluene/pressure ratio range of 2 to 6 is preferred.

Runs 7–10 show the effect of residence time in relation to Runs 1 through 3, and these runs show that the reduced residence time results in a slight decrease in byproduct formation. At concentrations of dinitrotoluene of less than about 2.5%, there is little change in byproduct formation at the reduced residence time.

Runs 16–28 show the effect of reactor geometry to the hydrogenation of dinitrotoluene and byproduct formation. The lower gas/liquid mass transfer coefficient of 1, which is on the low side of reactor design, shows that there is slightly greater byproduct formation relative to a reactor where the gas/liquid mass transfer coefficient is higher, i.e. 10. (Compare Run 21 to Run 5.) At a DNT inlet concentration of approximately 1.3% by weight, byproduct formation was substantially the same. (Compare Run 20 to Run 6.)

Runs 31–34 show the effects of catalyst activity on performance, and Runs 10 and 32 compare favorably and show that byproduct formation can be maintained at less than 1% by weight with excellent conversion.

To summarize, the results show that hydrogenation of dinitrotoluene on a continuous basis employing a reactor system containing a monolith catalyst can be safely utilized when operated under adiabatic conditions. The results show that dinitrotoluene concentrations greater than about 3% by weight generally result in excessive byproduct formation; e.g., greater than about 3% by weight even at higher pressures. Preferred feed concentrations appear to be from about 1 to 2% by weight and inlet temperatures ranges from about 100° to 140° C., with preferred ranges of from about 110° to 130° C. Pressures from 1600 to 8400 kP may be used. At these inlet temperatures and preferred feed concentrations, the adiabatic temperature rise within the reactor will range from about 25° to 50° C. which permits control over the reaction without excessive byproduct formation.

The results show that the monolith catalyst having a wash coat of palladium and nickel is effective in the continuous hydrogenation of dinitrotoluene. Under the conditions shown a single pass through the catalyst bed is sufficient to achieve dinitrotoluene conversions in excess of 95% and toluenediamine yields in excess of 98%.

The results also reveal that an isothermal process for the hydrogenation of DNT incorporating a catalyst of the type described herein would lead to excessive byproduct formation or extended cycle times or excessive reactor sizes.

What is claimed is:

1. In a process for hydrogenating a nitroaromatic composition by contacting said nitroaromatic composition with hydrogen in a reactor employing a monolith catalyst, the improvement for effecting continuous hydrogenation of dinitrotoluene to toluenediamine which comprises the steps:

(a) introducing a feedstock comprised of dinitrotoluene and reaction product components continuously into the reactor, (b) passing the feedstock through the reactor plug flow;

(c) carrying out the hydrogenation of dinitrotoluene to toluenediamine under adiabatic conditions; and, (d) continuously removing hydrogenated reaction product comprising unreacted dinitrotoluene, water and toluenediamine from the reactor.

2. The process of claim 1 wherein the concentration of dinitrotoluene in the feedstock to the reactor inlet ranges from to 0.2 to 3% by weight.

3. The process of claim 2 wherein the inlet temperature to the reactor is from 100° to 140° C.

4. The process of claim 3 wherein the exit temperature from the reactor is within a range from 135° to 170° C.

5. The process of claim 4 wherein the feedstock is comprised of dinitrotoluene and dinitrotoluene hydrogenation reaction product components, said feedstock having less than 10% by weight of a solvent other than said dinitrotoluene hydrogenation reaction products.

6. The process of claim 5 wherein the monolith catalyst has from 100 to 600 cells per square inch.

7. The process of claim 6 wherein the temperature rise through the reactor is within a range from 25° to 50° C.

8. The process of claim 7 wherein the residence time within the reactor system is from 10 to 120 seconds.

9. The process of claim 8 wherein the establishing and maintaining a ratio of from 2 to 6 ppm/total $H_2$ in kPa.

10. The process of claim 9 wherein the monolith catalyst has the catalytic metals nickel and palladium incorporated thereon.

11. The process of claim 1 wherein the exit temperature from the reactor is within a range from 145° to 165° C.

12. In a process for hydrogenating a nitroaromatic composition by contacting said nitroaromatic composition with hydrogen in a reactor employing a monolith catalyst, the improvement for effecting continuous hydrogenation of dinitrotoluene which resides in the steps:

(a) employing a monolith catalyst having sufficient activity to effect a reaction rate of hydrogenation of dinitrotoluene to toluenediamine of >2 gmoles $DNT/m^3$ catalyst second at a temperature of 1300° C. and a hydrogen pressure of 1600 kPa;

(b) establishing an inlet temperature of from 100° to 120° C.;

(c) continuously feeding hydrogen and a feed containing dinitrotoluene in an amount of from about 1 to 2% by weight plug flow through the high void volume monolith catalyst bed;

(d) continuously removing a toluenediamine/nitrotoluene reaction product from the monolith catalyst bed;

(e) maintaining a conversion of at least 90% of the feed dinitrotoluene to toluenediamine per pass through the monolith reactor; and, (f) recycling a portion of the toluenediamine/dinitrotoluene reaction product to the inlet of said high void volume catalyst bed.

13. The process of claim 12 wherein the ratio of dinitrotoluene in parts per million by weight divided by the hydrogenation pressure in kPa is from about 2 to 6.

* * * * *

UNITED STATES PATENT AND TRADEMARK OFFICE
Certificate

Patent No. 6,005,143

Patented: December 21, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Reinaldo Mario Machado, Allentown, PA; David Joseph Parrillo, Fleetwood, PA; Richard Peter Boehme, Allentown, PA; Robert Roger Broekhuis, Allentown, PA; and Gam Ananda Vedage, Bethlehem, PA.

Signed and Sealed this Twenty-first Day of February 2006.

JOSEPH K. MCKANE
*Supervisory Patent Examiner*
Art Unit 1626